United States Patent [19]

Kroll

[11] Patent Number: 5,407,444
[45] Date of Patent: Apr. 18, 1995

[54] STAGED ENERGY CONCENTRATION FOR A DEFIBRILLATOR

[75] Inventor: Mark W. Kroll, Minnetonka, Minn.

[73] Assignee: Angeion Corporation, Plymouth, Minn.

[21] Appl. No.: 993,094

[22] Filed: Dec. 18, 1992

[51] Int. Cl.6 ................................. A61N 1/39
[52] U.S. Cl. ............................... 607/5; 320/3
[58] Field of Search ................. 607/5; 320/3

[56] References Cited

U.S. PATENT DOCUMENTS 3,959,706  5/1976  Mabuchi et al. .............. 320/3
4,736,150  4/1988  Wagner ........................ 320/21
5,235,979  8/1993  Adams ......................... 607/5

Primary Examiner—William E. Kamm
Assistant Examiner—Scott M. Getzow
Attorney, Agent, or Firm—Patterson & Keough

[57] ABSTRACT

A system and method of power delivery to a main countershock electrical circuit in an implantable defibrillator comprises a staged energy configuration. Monitoring and control elements cooperate with staged batteries. The batteries comprise a first, non-rechargeable battery and a second, rechargeable battery for rapidly recharging a defibrillation capacitor.

18 Claims, 2 Drawing Sheets

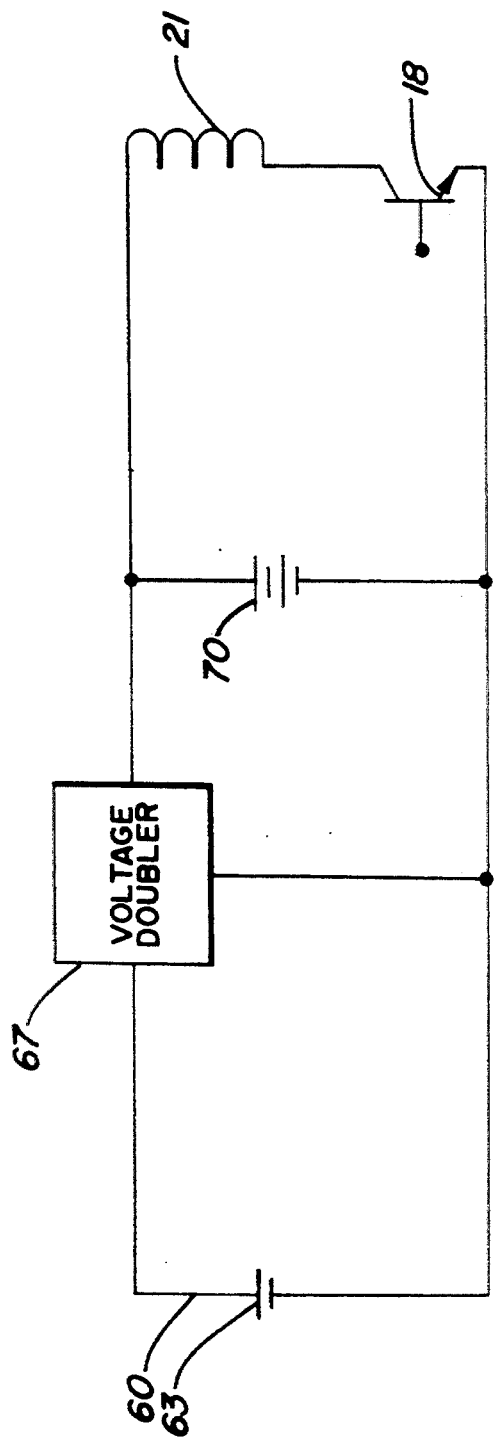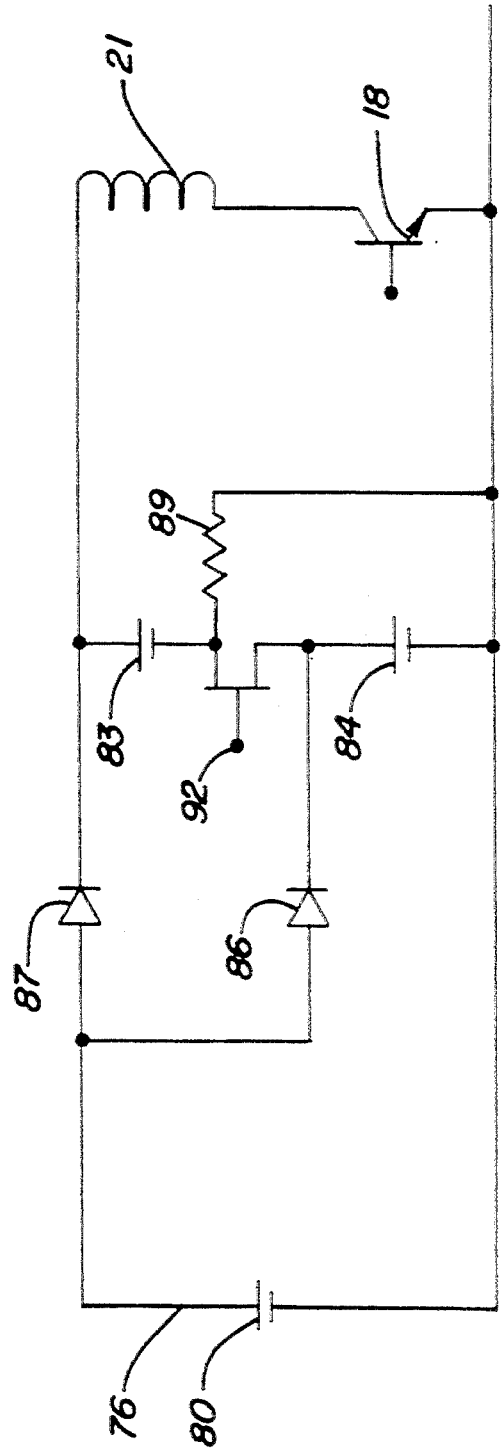
FIG. 3
FIG. 4

STAGED ENERGY CONCENTRATION FOR A DEFIBRILLATOR

FIELD OF THE INVENTION

This invention relates to the power supply for an implantable defibrillator, and more particularly to use of a rechargeable battery for rapidly recharging a defibrillation capacitor.

BACKGROUND OF THE INVENTION

Cardiac defibrillation in humans requires the delivery of an electrical pulse that is several milliseconds long with peak currents as high as 25 amperes. The total energy in such a pulse is about 30 Joules. In order to deliver such a high current, a capacitor is charged up to a voltage on the order of 750 volts.

Various special batteries have been developed to supply such a high current to charge the capacitor. However, the batteries in use comprise low energy density batteries which occupy a large volume within the defibrillator. In defibrillator devices, the combined volume of the battery and the capacitor(s) is greater than the electronics. Therefore, any reduction in battery size or weight provides significant enhancements to an implantable defibrillator.

SUMMARY OF THE INVENTION

An implantable defibrillator, and method of operation, is provided which comprises monitoring and control means and battery means for powering the monitoring and control means, and for providing defibrillation pulses. The battery means comprises a first, non-rechargeable battery and a second, rechargeable battery for rapidly recharging a defibrillation capacitor.

A staged energy delivery system for an implantable defibrillator is also provided. The staged energy delivery system comprises a first stage of energy concentration comprising a non-rechargeable battery, and a second stage of energy concentration comprising rechargeable battery means for rapidly charging storage and discharge capacitance means.

Another embodiment of an energy delivery system for an implantable defibrillator is provided. This embodiment comprises a first stage of energy concentration comprising a non-rechargeable battery, and a second stage of energy concentration comprising rechargeable battery means. The rechargeable battery means is configured for providing energy to a capacitor so that defibrillation pulses are readily available for use by the implantable defibrillator.

BRIEF DESCRIPTION OF THE DRAWINGS

FIG. 3 is a simplified schematic circuit diagram of an alternate embodiment staged energy concentration circuit.

FIG. 4 is a simplified schematic circuit diagram of an alternate embodiment staged energy concentration circuit.

DETAILED DESCRIPTION OF THE INVENTION

Figure 1:
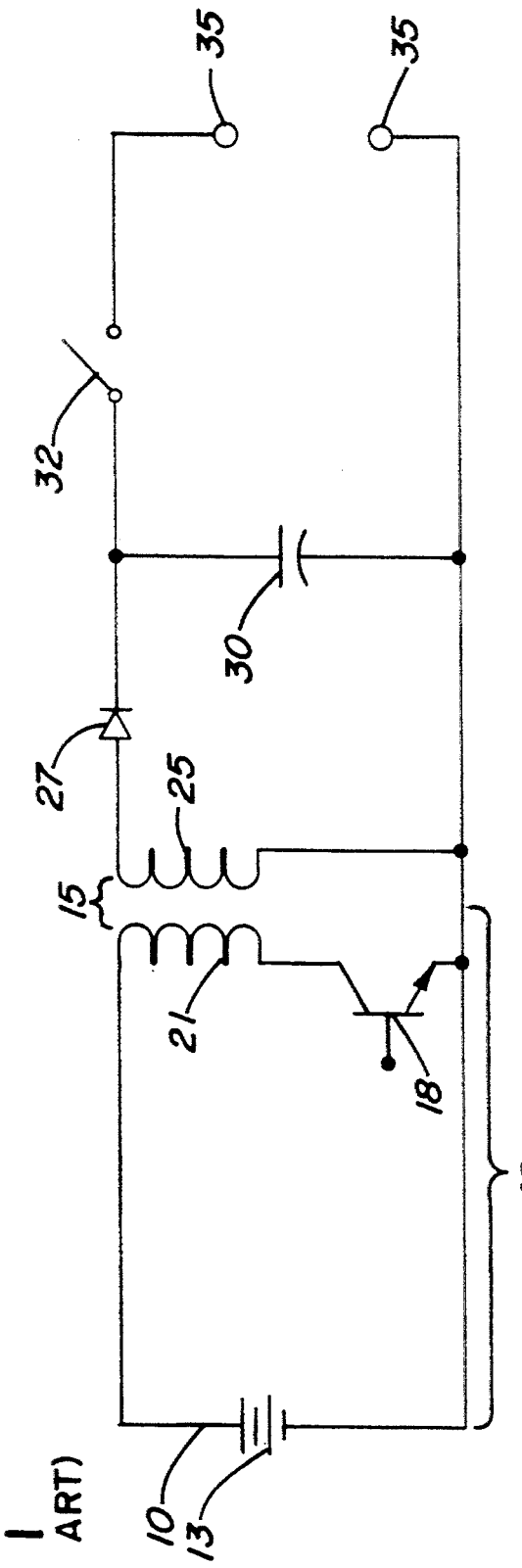
FIG. 1 is a simplified circuit diagram of a prior art implantable defibrillator circuit.

FIG. 1 is a simplified circuit diagram of a known implantable defibrillator circuit 10. Circuit 10 comprises a high current defibrillation battery 13, which is typically a lithium silver vanadium pentoxide ($LiAgVO_5$) battery. A high voltage transformer 15 comprises a transistor switch 18 which drives the primary 21. The oscillator driving switch 18 provides an alternating current through the primary of transformer 15. The secondary 25 of transformer 15 produces a significantly higher voltage which is rectified by diode 27 and stored in capacitor 30. When capacitor 30 is fully charged, the semiconductor switch 32 is activated to complete the circuit which delivers the charge of capacitor 30 to the cardiac electrodes 35 for defibrillation of the heart. A configuration which is similar to the above circuit comprises substitution of a H-bridge in place of switch 32. This permits delivery of the current from capacitor 30 in either polarity, which allows delivery of a biphasic pulse.

Circuit 10 works well in cardiac defibrillators. However, the $LiAgVO_5$ batteries have an energy storage density of only 500 Joules per gram (J/g). This is due to the tradeoff between energy storage capability and current delivery capability. In contrast, the battery chemistry of the well known Lithium Iodide (LiI) pacemaker battery has approximately twice the energy storage density of the $LiAgVO_5$ battery, or about 1000 J/g. This means that defibrillator devices using a $LiAgVO_5$ battery are utilizing a battery with a mass that is twice that which could be used if a LiI pacemaker battery were used. However, use of a LiI battery alone would result in delivery of only very small currents, on the order of milliamps. Therefore, as disclosed in copending U.S. patent application Ser. No. 670,188, it is possible to use an LiI battery to power monitoring and integration circuits/related systems, and a $LiAgVO_5$ to charge a capacitor sub-system.

Figure 2:
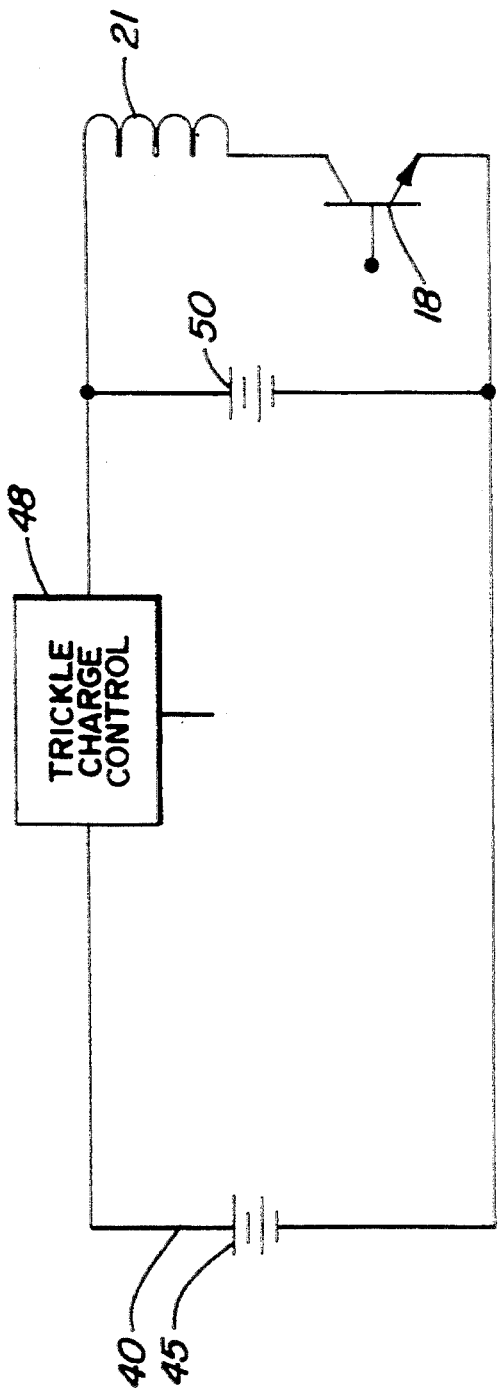
FIG. 2 is a simplified schematic circuit diagram of a staged energy concentration circuit.

FIG. 2 discloses a simplified schematic staged energy circuit 40. Circuit 40 comprises a first embodiment of an improved staged energy concentration means designed for replacing that portion of circuit 10 denoted as primary sub-circuit 42 in FIG. 1. Circuit 40 preferably comprises a first stage of energy concentration comprising a non-rechargeable battery, such as a high energy density pacing battery 45, configured for applying a small microampere current to the trickle charge control circuitry 48. This provides an optimum current to be supplied to a second stage of energy concentration, comprising at least rechargeable battery means. The rechargeable battery means preferably comprises a rechargeable defibrillator battery 50 and is maintained fully charged by the pacing battery 45. Rechargeable defibrillator battery 50 is used to drive primary 21 of the high voltage transformer, or similar power transfer means, through a switch 18 in a manner similar to conventional circuits, such as circuit 10.

The staged energy concentration configuration of circuit 40 permits use of high density pacing batteries to store energy in combination with a very small rechargeable defibrillator battery to deliver a high current for up to about 10 shocks. A typical defibrillator will deliver about 200 defibrillator shocks. Assuming each of the shocks is of 30 Joules, and with transformer losses of 25%, the energy system must store $200 \times 40 \text{ J} = 8000$ Joules. However, due to this staged energy arrangement, the rechargeable battery need only store enough energy for a typical cardiac defibrillation session of about 5 shocks. The battery means comprising the second stage of energy concentration must therefore only store about 5×40 J=200 Joules. Although this is very little energy, the second stage battery means must be able to deliver a fairly high current of about 1–2 amperes. Representative battery chemistries capable of meeting these specifications are shown in Table 1.

TABLE 1

| Second Stage Batteries | |
|---|---|
| Chemistry | Average Voltage |
| $LiMoS_2$ | 1.85 |
| $LiMnO_2$ | 3.0 |
| $LiV_2O_5$ | 2.8 |
| $LiTiS_2$ | 2.2 |
| $LiV_6O_{13}$ | 2.3 |
| $LiCuC_{12}$ | 3.2 |
| $LiSO_2$ | 3.1 |

FIG. 3 discloses another embodiment of the staged energy concentration invention. Circuit 60 discloses a single cell pacing battery 63 which is used to power a voltage doubler circuit 67. This doubler circuit 67, which comprises numerous embodiments, may be configured to produce an output of approximately 6 volts for charging a rechargeable defibrillation battery, such as battery 70.

Another embodiment of a staged energy concentration defibrillator circuit is shown in FIG. 4, in which circuit 76 comprises first stage battery 80. Battery 80 is a low voltage, for example a 2.8 volt, LiI single cell battery which charges two second stage batteries 83 and 84. Batteries 83, 84 are preferably Lithium Titanium Disulfide ($LiTiS_2$) batteries. Preferably, battery 84 is charged through diode 86, battery 83 is charged through diode 87, and resistor 89 is used with a preferred value of 10K ohms. Field effect transistor switch 92 is off during this time. It is recognized that this schematic circuit is further simplified because there is optimal trickle charge current limiting between battery 80 and the two diodes, however, that detail is not considered important to this depiction of the invention.

When fibrillation is detected by related detection circuitry, it is then time to charge the defibrillation capacitor(s) and switch 92 is turned on. That places batteries 83 and 84 in series, providing a voltage of approximately 5 volts for the transformer primary 21. As above, oscillating switch 18 is used to cause a pulsating current to pass through primary 21 of the transformer.

Use of a multi-stage energy concentration defibrillator, as disclosed in FIGS. 2–4, provides great savings in both volume and weight of the defibrillator. For example, since the defibrillator battery chemistry has about half the density of the pacing battery, it is possible to reduce the total battery weight and volume by greater than about 50%. This provides dramatic improvement in the manufacture, implantation, and operation of the defibrillator, particularly in view of the restricted size of desired pectoral implant sites.

The invention further comprises a multi-stage energy concentration technique for a defibrillator in which the defibrillator capacitor means comprises either a third stage or a secondary sub-circuit of the second stage. In either configuration, it is advantageous to provide a rechargeable second stage or intermediate battery means as a fully charged high current output battery means. This permits rapid charging of the defibrillator capacitor means. Indeed, in certain configurations it is now possible to recharge at a rapid 3–5 second rate using this invention rather than at a slower rate, which is common in the industry. Therefore, yet another advantage of this invention derives from the use of the second stage energy concentration as a recharge rate accelerator. This also results in a defibrillator with reduced end of life charge degradation due to the constantly recharged second stage. This feature effectively provides a battery life extension capability before elective replacement, assuming certain accepted energy levels.

I claim:

1. An implantable defibrillator for delivering electrical defibrillation pulses to a plurality of implanted electrodes proximate a heart of a human patient for treating a ventricular fibrillation, comprising:

monitoring means for electrically monitoring the heart for an occurrence of ventricular fibrillation;

charge storage means for storing an electrical defibrillation pulse to be delivered to the plurality of implanted electrodes;

control means for controlling the charging and discharging of the charge storage means in response to each occurrence of ventricular fibrillation; and battery means for powering the monitoring and control means and for providing the electrical energy for charging the charge storage means, the battery means comprising a first, non-rechargeable battery and a second, rechargeable battery for rapidly recharging the charge storage means.

2. A staged energy delivery system for an implantable defibrillator, comprising:

discharge capacitance means for charge storage;

a first stage of energy concentration comprising a non-rechargeable battery; and a second stage of energy concentration comprising a rechargeable battery means for rapidly charging the discharge capacitance means the discharge capacitance means and the first stage and second stage of energy concentration all being contained within the implantable defibrillator.

3. The energy delivery system of claim 2 in which the non-rechargeable battery comprises a high energy density primary battery having at least one cell.

4. The energy delivery system of claim 2 in which the rechargeable battery means comprises at least one high current output rechargeable battery.

5. The energy delivery system of claim 2 in which the non-rechargeable battery charges the rechargeable battery means.

6. The energy delivery system of claim 2 in which the rechargeable battery means is selected from a list of battery means having compositions comprising $LiMOS_2$, $LiMnO_2$, $LiV_2O_5$, $LiTiS_2$, $LiV_6O_{13}$, $LiCuC_{l2}$, and $LiSO_2$.

7. An energy delivery system for an implantable defibrillator, comprising:

capacitor means for energy storage;

a first stage of energy concentration comprising a non-rechargeable battery; and a second stage of energy concentration comprising a rechargeable battery means for providing energy to the capacitor means so that defibrillation pulses are readily available for use by the implantable defibrillator, the capacitor means, the first stage of energy concentration and the second stage of energy concentration all being contained within the implantable defibrillator.

8. The energy delivery system of claim 7 in which the non-rechargeable battery comprises a pacing battery.

9. The energy delivery system of claim 8 in which the pacing battery is a single cell pacing battery.

10. The energy delivery system of claim 9 in which the single cell pacing battery is a lithium iodide battery.

11. The energy delivery system of claim 7 in which the rechargeable battery means comprises a plurality of low energy high current batteries.

12. The energy delivery system of claim 11 in which the low energy high current batteries are lithium titanium disulfide batteries.

13. The energy delivery system of claim 11 further comprising a step-up transformer in which the low energy high current batteries are electrically configured for series discharge to a primary coil side of the step-up transformer to selectively and quickly charge the capacitor means.

14. The energy delivery system of claim 7 in which the non-rechargeable battery continuously charges the rechargeable battery means.

15. The energy delivery system of claim 7 in which the rechargeable battery means recharges the capacitor means in less than about 6 seconds.

16. A method of providing staged energy delivery in an implantable defibrillator having a main countershock electrical circuit including a discharge capacitor, the method comprising the steps of:

providing a first stage of energy concentration using a non-rechargeable battery electrically connected to the main countershock electrical circuit; and arranging a second stage of energy concentration using a rechargeable battery means electrically connected in parallel to the non-rechargeable battery for providing electrical energy to the main countershock electrical circuit so that defibrillation countershock pulses are readily available for use by the implantable defibrillator.

17. The method of claim 16 further comprising the step of continuously recharging the rechargeable battery means from the non-rechargeable battery.

18. The method of claim 16 in which the rechargeable battery means comprises a plurality of low energy high current batteries.

* * * * *